United States Patent [19]

Pigerol et al.

[11] E Re. 30,655

[45] Reissued Jun. 23, 1981

[54] PROCESS FOR PREPARING 3-THIENYL-ACETATE DERIVATIVES

[75] Inventors: Charles Pigerol; Marie-Madeleine Chandavoine; Michel Chignac; Paul de Cointet de Fillain, Sisteron, all of France

[73] Assignee: Labaz, Paris, France

[21] Appl. No.: 163,500

[22] Filed: Jun. 27, 1980

Related U.S. Patent Documents

Reissue of:

[64] Patent No.: 4,186,137
Issued: Jan. 29, 1980
Appl. No.: 778,498
Filed: Mar. 17, 1977

U.S. Applications:

[63] Continuation-in-part of Ser. No. 651,174, Jan. 21, 1976, abandoned, which is a continuation of Ser. No. 549,938, Feb. 14, 1975, abandoned, which is a continuation-in-part of Ser. No. 501,855, Aug. 29, 1974, abandoned.

[30] Foreign Application Priority Data

Aug. 30, 1973 [FR] France ..... 73 31321

[51] Int. Cl.[3] ..... C07D 333/16
[52] U.S. Cl. ..... 549/79
[58] Field of Search ..... 549/79

[56] References Cited

U.S. PATENT DOCUMENTS

| | | | |
|---|---|---|---|
| 3,755,412 | 8/1973 | Taranko | 260/465 |
| 3,832,354 | 8/1974 | Gadient | 549/79 |

*Primary Examiner*—Alan Siegel
*Attorney, Agent, or Firm*—Mason, Kolehmainen, Rathburn & Wyss

[57] ABSTRACT

3-Thienyl-acetate derivatives of the general formula:

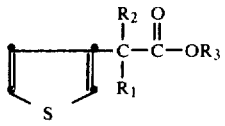

wherein $R_1$ represents an alkyl, a cycloalkyl or an aralkyl radical, $R_2$ represents hydrogen or $R_1$ and $R_2$, when they are taken together to form a cyclic group with the carbon atom to which they are attached, represent a polymethylene radical having from 2 to 5 carbon atoms, are prepared from a mixture consituted by a compound of the formula:

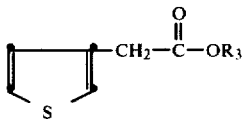

wherein $R_3$ has the meaning given above and an organic halide of the formula:

$R_4X$ wherein X represents fluorine, chlorine, bromine or iodine and $R_4$ represents an alkyl, cycloalkyl or aralkyl radical or $—CH_2(CH_2)_nX$ in which n is an integer in the range of from 1 to 4 inclusive and X has the meaning given above, which mixture is added to an alkali metal hydride in dimethylformamide, at a temperature between −20° C. and −5° C., and allowed to react, in one step, at a temperature between −20° C. and −5° C.

The 3-thienyl-acetate derivatives of formula I are useful as intermediate products for preparing pharmacologically active compounds.

1 Claim, No Drawings

PROCESS FOR PREPARING 3-THIENYL-ACETATE DERIVATIVES

Matter enclosed in heavy brackets [ ] appears in the original patent but forms no part of this reissue specification; matter printed in italics indicates the additions made by reissue.

CROSS-REFERENCE TO RELATED APPLICATIONS

This application *is a reissue of application Ser. No. 778,498 now U.S. Pat. No. 4,186,137 which* is a continuation-in-part of application Ser. No. 651,174 filed Jan. 21, 1976 now abandoned which is a continuation of Ser. No. 549,938 filed Feb. 14, 1975 now abandoned which is a continuation-in-part of Ser. No. 501,855 filed Aug. 29, 1974 now abandoned.

This invention relates to a process for preparing thiophene derivatives.

The thiophene derivatives prepared by the process of the invention are the alkyl 3-thienyl-acetate derivatives corresponding to the general formula:

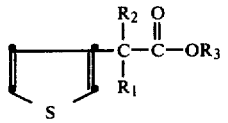

I wherein $R_1$ represents an alkyl radical preferably ethyl, a cycloalkyl radical, preferably cyclohexyl, or an aralkyl radical, preferably benzyl, $R_2$ represents an atom of hydrogen, or $R_1$ and $R_2$, when they are taken together to form a cyclic group with the carbon atom to which they are attached, represent a polymethylene radical having from 2 to 5 carbon atoms, preferably tetramethylene or pentamethylene, and $R_3$ represents an alkyl radical preferably methyl or ethyl.

Following one aspect of the invention, there is provided a method for preparing methyl or ethyl α-(3-thienyl)-α-cyclohexyl-acetate.

It is already known that certain 3-thienyl-acetic acid esters mono-substituted in the α-position possess particularly valuable pharmacological properties. A class of such 3-thienyl-acetic ester derivatives has been published and described in French BSM No. 5504 M as being capable of treating spasmodic and painful states of the digestive, biliary and urinary tracts, of the arterio-venous system and of the pelvic organs.

One of the best known compounds of this series is β-N-hexamethyleneiminoethyl ester of 2-cyclohexyl-3-thienyl-acetic acid of which the generic name is cetiedil.

Cetiedil has proved to be very useful as an anti-ischemia and peripheral vasoregulator agent and may be considered as being, presently, the most effective agent for the treatment of peripheral arterial diseases (Lille Medical. Actualites 3eme Serie, Tome XVIII, pp. 1303-1312—1973).

U.S. Pat. No. 2,685,589 discloses 3-thienyl-acetic esters bearing a cyclopolymethylene incorporating the α-carbon. These esters are described as possessing anti-spasmodic activity and more particularly an antispasmodic action on normal smooth muscle as well as against neurotropic and musculotropic spasms of smooth muscle. These compounds are also useful as antifungal agents.

However, the processes known up to present for the preparation of cetiedil and the other esters hereabove cited are far from satisfactory when applied on the industrial scale.

The prior processes are generally relatively complicated and involve in particular reactions which must be maintained at very low temperatures, usually below −50° C., by means of reagents which are both costly and difficult to obtain through ordinary trade channels. Furthermore, to obtain the end-product a fairly large number of intermediary stages must be gone through counting from the commercially available starting thiophene. In addition, certain intermediary steps must be performed by means of a reaction involving the use of organo-metallic derivatives, which is of course a very delicate reaction to carry out on the industrial scale since it requires the use of anhydrous ethers which are generally very volatile. These methods are also most unrewarding if account is taken of the care and effort which must go into their use. In view of this disadvantage and of those listed above, the processes so far known can only be suitable for laboratory work and could not be usefully applied on the industrial scale.

As an example of such processes which it would be difficult to employ on the industrial scale, mention may be made of that described in U.S. Pat. No. 2,685,589 for the preparation of thienyl-acetic esters di-substituted in the α-position, a process which could also be used for preparing the α-substituted derivatives as well.

As will be shown further on in detail, the process of the invention does, in fact, provide a means of obtaining the esters of formula I which is very simple and consequently markedly superior to what is known up to present.

An example of the method which is widely used for alkylating acetic esters in the α-position is given in column 1 of U.S. Pat. No. 3,755,412.

The alkylation in question may be effected by heating the appropriate acetic ester with a strong base such as sodium hydride and reacting the resultant alkali salt with an organic halide. Different organic solvents can be used in this process including liquidammonia, alcohols, ethers and aromatic hydrocarbons.

The process described hereabove using dimethylformamide as solvent is disclosed and exemplified in U.S. Pat. No. 3,832,354 for the preparation of 4-hydroxy-5-phenyl-3-thiophene acetic acids and derivatives thereof.

In the course of trials undertaken with a view to preparing 3-thienyl-acetic ester derivatives of formula I, this aforesaid process was applied.

Thus, the required 3-thienyl-acetic ester of formula I was prepared in accordance with this process by first heating an alkyl 3-thienyl-acetate with sodium hydride in dimethylformamide and then reacting the alkali metal salt so produced by heating it with the appropriate halide. The operative conditions and specific temperatures employed were those described in U.S. Pat. No. 3,832,354 (Example 216).

Following this procedure, methyl α-(3-thienyl)-α-cyclohexyl-acetate was obtained in a yield of only 36%.

However, it was unexpectedly found, in accordance with the present invention, that it is possible to improve considerably this process of preparation of the alkyl 3-thienyl-acetate derivatives of formula I by modifying the order of introduction of certain reagents, and in particular by adding to the reaction medium the starting acetic acid ester and the halide not separately but premixed, and by effecting this operation of addition at a given range of temperatures.

In fact, it has been quite surprisingly discovered that the temperature of the reaction medium to which the mixture of starting ester and organic halide is added is of considerable importance with respect to the yield in final compound of formula I.

Thus, it has been found that when the temperature of the reaction medium is maintained below 0° C. during all the period of introduction of the mixture of starting ester and halide, the yield in final 3-thienyl acetic ester of formula I is considerably increased.

Similarly, it has been found that no heating is necessary after the mixture of starting ester and halide is added, the reaction medium being maintained for several hours at the temperature used during the introduction of the mixture of starting ester and halide.

According to the invention, the thiophene derivatives of formula I are prepared from a mixture constituted by a compound of the formula:

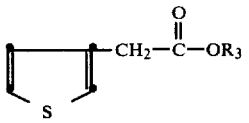

II wherein $R_3$ has the same meaning as in formula I and an organic halide of the formula:

$R_4X$ III wherein X represents an atom of fluorine, chlorine, bromine or iodine, preferably chlorine, bromine or iodine and $R_4$ represents an alkyl radical, preferably ethyl, a cycloalkyl radical, preferably cyclohexyl, an aralkyl radical, preferably benzyl, or a $-CH_2(CH_2)_nX$ radical in which n is an integer in the range of from 1 to 4 inclusive, preferably 3 or 4, and X has the meaning given above, which mixture is added to an alkali metal hydride, preferably sodium hydride, in dimethylformamide at a temperature between −20° C. and −5° C. and allowed to react in one step at a temperature between −20° C. and −5° C.

As a preferred value for $R_4$, cyclohexyl can be cited. Similarly, bromine is the preferred value for X.

Following one aspect of the invention methyl or ethyl α-(3-thienyl)-α-cyclohexyl-acetate is prepared by adding, at a temperature of −15° C., a mixture of methyl or ethyl 3-thienyl-acetate and cyclohexyl bromide to an alkali metal hydride, preferably sodium hydride, in dimethylformamide and allowing the reaction to occur, in one step, at a temperature between −15° C. and −10° C. to obtain methyl or ethyl α-(3-thienyl)-α-cyclohexyl-acetate.

In accordance with known chemical procedures and when it is desired to substitute the alkyl 3-thienyl-acetate in the α,α-positions namely to introduce a cyclopolymethylene radical, the alkyl 3-thienyl-acetate in question is treated so that at least two molar equivalents of the appropriate halide of formula III, preferably in excess, react with one molar equivalent of alkyl 3-thienyl-acetate.

When it is desired to place one single substituent in the α-position of the alkyl 3-thienyl-acetate, the latter compound is treated so that one molar equivalent of the appropriate halide of formula III reacts with one molar equivalent of alkyl 3-thienyl-acetate.

The esters of formula II may be prepared by known procedures and, in particular, by esterifying the corresponding 3-thienyl-acetic acids which are known compounds or one of their halides, such as the chloride, by means of an alcohol of the general formula $R_3OH$ in which $R_3$ has the same meaning as in formula I.

The halides of formula III are known compounds.

As stated above, the process of the invention presents valuable advantages over the process described in U.S. Pat. Nos. 3,755,412 and 3,832,354.

It is possible with the process of the invention to increase the yield in thiophene derivatives of formula I obtained by the process cited in the U.S. Patents in question.

A summary is given hereunder of trials undertaken in accordance with the known processes in comparison with the process of the invention.

In this connection, methyl α-(3-thienyl)-α-cyclohexyl-acetate was prepared.

The starting compounds were the following:

31.2 g of methyl α-(3-thienyl)-acetate (I)
42.4 g of cyclohexyl bromide (II)
180 ml of dimethylformamide (III)
4.6 g of sodium hydride (IV)

A. First trial

The method used was that described in Example 216 of U.S. Pat. No. 3,832,354.

Into a flask, (III) and (IV) were introduced.

While stirring, a solution of (I) in 10 ml of dimethylformamide was added at room-temperature. The operation lasted 15 minutes and the temperature rose from 25° C. to 34° C.

The mixture was then heated for 30 minutes at 60° C. after which it was cooled to +2° C.

Over a period of 10 minutes, a solution of (II) in 10 ml of dimethylformamide was added to the reaction medium which was no longer cooled. The final temperature was 4° C.

The temperature was allowed to increase and the mixture was stirred at room-temperature for 100 minutes and then heated to 60° C. for 20 minutes. The mixture was cooled, poured into 300 ml of iced water and extracted with 4 fractions, each of 100 ml, of ethyl ether. The ethereal fractions were washed with water, dried on magnesium sulphate and concentrated under vacuum.

The crude oil (40 g) so obtained was rectified by distillation first under 15 mm Hg and then under 0.7 mm Hg and 17 g of pure product were obtained.

Yield in methyl α-(3-thienyl)-α-cyclohexyl-acetate compared with the starting ester: 36%.

B. Second trial

The method used was that described in Example 216 of U.S. Pat. No. 3,832,354 but the temperature of reaction was lowered (column 6, lines 70 and 71 of this U.S. Patent).

Into a flask, (III) and (IV) were introduced.

While stirring, a solution of (I) in 10 ml of dimethylformamide was added at room-temperature. The operation of addition lasted 15 minutes and the temperature rose from 25° C. to 34° C.

The mixture was then heated for 30 minutes at 60° C. after which it was cooled to −15° C.

Over a period of 45 minutes, a solution of (II) in 10 ml of dimethylformamide was added to the reaction medium. Stirring was maintained for 3 hours and the temperature was allowed to return to 20° C. Three hours later, the mixture was poured into 300 ml of iced water and extracted with 4 fractions, each of 100 ml, of ethyl ether.

The ethereal fractions were then treated as in the first trial.

Yield in methyl α-(3-thienyl)-α-cyclohexyl-acetate compared with the starting ester: 34.8%.

C. Third trial

The method used was that of the present invention.

Into a flask, (III) and (IV) were introduced.

The medium was cooled to −15° C. and a solution of (I) and (II) in 20 ml of dimethylformamide was added. The operation lasted 45 minutes.

Stirring was then maintained for 3 hours.

When no more hydrogen was given off i.e. 2 to 4 hours later, the reaction medium was hydrolysed with 300 ml of iced water and extracted with 4 fractions, each of 100 ml, of ethyl ether.

The ethereal fractions were then treated as in the first trial.

Yield in methyl α-(3-thienyl)-α-cyclohexyl-acetate compared with the starting ester: 52%.

These results show that the process of the invention is superior to that of the state of the art.

Another trial was made using the specific order of introduction of the reagents in accordance with the process of the invention but employing other ranges of temperatures.

D. Fourth trial

Into a flask, (III) and (IV) were introduced.

The medium was cooled to +2° C. and cooling was suspended. After that, a solution of (I) and (II) in 20 ml of dimethylformamide was added. The operation lasted 15 minutes. The final temperature of the reaction medium was 30° C. with an intermediate increase to 58° C.

Stirring was then maintained at room-temperature for 100 minutes and the medium was heated to 60° C. for 20 minutes. The mixture was cooled, poured into 300 ml of iced water and extracted with 4 fractions, each of 100 ml, of ethyl ether.

The ethereal fractions were then treated as in the first trial.

Yield in methyl α-(3-thienyl)-α-cyclohexyl-acetate compared with the starting ester: 29.4%.

This result demonstrates the important role of the temperature in the process of the invention.

In addition to the better yield in compound of formula I provided with the process of the invention, there are other advantages.

The process of the invention can be conducted in only one single step i.e. the addition of premixed alkyl 3-thienyl-acetate and halide of formula III to the reaction medium. As against this, the process cited in U.S. Pat. Nos. 3,755,412 and 3,832,354 requires first that the alkyl 3-thienyl-acetate be added to and heated with the reaction medium and secondly that the halide of formula III be subsequently added to the resulting salt.

With the process of the invention it is consequently possible to reduce to the maximum degree the calorific energy which is necessary to ensure the reaction and to gain time which is very important when a process is applied on the industrial scale.

Thus, it may be concluded that the thiophene derivatives of formula I, when prepared in accordance with the process of the invention, constitute by virtue of the ease with which they are prepared, particularly useful intermediate products for obtaining the pharmacologically valuable thiophene derivatives mentioned above.

These pharmacologically valuable thiophene derivatives will be prepared easily by trans-esterification of the corresponding alkyl 3-thienyl-acetates in accordance with known chemical procedures.

The preparation of the thiophene derivatives following the process of the invention is illustrated by the non-limitative Examples which follow:

EXAMPLE 1

Preparation of ethyl α-(3-thienyl)-α-cyclohexyl-acetate

In a 500 ml-flask fitted with a mechanical stirrer, a condenser protected by a calcium chloride stopper, a dropping funnel and a source of nitrogen, were placed 250 ml of dimethylformamide and 8 g (0.33 mol) of sodium hydride. The reaction medium was cooled to −15° C. and then a mixture of 51 g (0.3 mol) of ethyl 3-thienyl-acetate and 53 g (0.33 mol) of cyclohexyl bromide was added under nitrogen atmosphere. Stirring was maintained for 3 hours at −10° C. and then the reaction medium was allowed to return to 20° C. When hydrogen ceased to be given off, i.e. from 2 to 4 hours later, the reaction medium was hydrolyzed with 500 ml of iced water. The aqueous solution was extracted with 500 ml ether, the ethereal phase was washed with water and dried. The solution was concentrated under reduced pressure and the residue so obtained was distilled under reduced pressure.

In this manner, 64 g of ethyl α-(3-thienyl)-α-cyclohexyl-acetate were obtained which represents a yield of 80%.

B.P. 140° C. under 3 mm Hg.

By following the same procedure as that described hereabove but using the appropriate starting-products, the compound hereunder was prepared:

| Compound | Boiling point in °C. |
|---|---|
| Methyl α-(3-thienyl)-α-cyclohexyl-acetate (Yield : 83%) | 130 (1 mm Hg) |

EXAMPLE 2

Preparation of ethyl α-(3-thienyl)-α-ethyl-acetate

In a 250 ml-flask equipped as in Example 1, hereabove, were introduced 2.4 g (0.1 mol) of sodium hydride and 70 ml of dimethylformamide.

The reaction medium was cooled to −20° C. and then a mixture of 17 g (0.1 mol) of ethyl 3-thienyl-acetate and 10 g (0.99 mol) of ethyl bromide were added, drop-by-drop, care being taken that the temperature did not exceed −10° C. This operation lasted 2 hours. The temperature was maintained at −10° C. for a further 2 hours and then the reaction mixture was allowed to return to room-temperature. Stirring was maintained for 12 hours after which the reaction medium was hydrolyzed with 100 ml of iced water. The aqueous phase was extracted twice with 100 ml of ether and the ethereal phase was washed with water, dried and concentrated. The residue so formed was finally distilled under reduced pressure.

In this manner, 12 g of ethyl α-(3-thienyl)-α-ethyl-acetate were obtained which represents a yield of 65%. B.P. 96° C. under 3 mm Hg.

EXAMPLE 3

Preparation of ethyl α-(3-thienyl)-α-benzyl-acetate

In a 250-ml-flask fitted as in Example 1, hereabove, were placed 2.4 g of a suspension of sodium hydride in 70 ml of dimethylformamide. The temperature of the flask was lowered to −15° C. and then a mixture of 8 g of ethyl 3-thienyl-acetate and 6.3 g of benzyl chloride was added, drop-by-drop, so that the temperature never rose above −10° C. This operation was effected in about 30 minutes during which time hydrogen was given off. If the escape of hydrogen was not terminated at the end of the operation of adding the mixture, the temperature of the reaction medium was maintained at −10° C. for a further hour. The mixture was then allowed to return to room-temperature and stirring was maintained for 12 hours. Drop-by-drop, 70 ml of water were then introduced and the mixture was extracted with ether. The ethereal phase was washed with water, dried and distilled.

In this manner, 4 g of ethyl-α-(3-thienyl)-α-benzyl-acetate were obtained which represents a yield of 15%. B.P. 140° C. under 2 mm Hg.

EXAMPLE 4

Methyl-α-(3-thienyl)-α-benzylacetate can be produced by the procedure of Example 3, by substituting methyl 3-thienyl-acetate for ethyl 3-thienyl-acetate, all the other conditions being the same.

EXAMPLE 5

Preparation of methyl α-(3-thienyl)-αα-cyclotetramethylene acetate

In a one-liter-flask fitted as in Example 1, hereabove, were placed 300 ml of dimethylformamide and 9.8 g (0.41 mol) of sodium hydride. The temperature of the flask was lowered to −10° C. and then, under nitrogen atmosphere, a solution of 31.2 g (0.2 mol) of methyl 3-thienyl-acetate and 64.8 g (0.3 mol) of 1,4-dibromobutane in 60 ml of dimethylformamide was added, care being taken to stir vigorously and maintain the temperature between −10° C. and −5° C. for the first 90 minutes. This operation of addition was effected in about 2 hours. The reaction medium was then poured into 500 ml of iced water and extracted with twice 200 ml of ethyl ether. The ethereal phases were collected, washed with water, dried and concentrated under reduced pressure. The crude product so obtained was then distilled under reduced pressure. The fraction boiling at 100° C. under 0.3 mm Hg was collected, whereupon it solidified. In this manner 32 g of methyl α-(3-thienyl)-αα-cyclotetramethylene acetate were obtained which were recrystallized from pentane, representing a yield of 70%.

M.P. 49° C.

By following the same procedure as that described above but using the appropriate starting-products, the compound hereunder was prepared:

| Compound | Boiling point in °C. |
|---|---|
| Methyl α-(3-thienyl)-αα-cyclopentamethylene acetate | 120° C. (0.5 mm Hg) |

We claim:

1. In a process for the preparation of a thiophene compound corresponding to the formula:

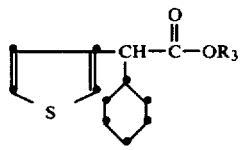

wherein $R_3$ represents methyl or ethyl, by the reaction in one step between methyl or ethyl 3-thienyl-acetate and cyclohexyl bromide at a temperature between −15° C. and −10° C. in the presence of sodium hydride in dimethylformamide, the improvement which comprises:

(a) premixing said methyl or ethyl 3-thienyl-acetate with cyclohexyl bromide, and (b) adding at −15° C. said methyl or ethyl 3-thienyl-acetate/cyclohexyl bromide mixture to said mixture of sodium hydride in dimethylformamide.

* * * * *